(12) United States Patent
Heitai et al.

(10) Patent No.: US 8,329,210 B2
(45) Date of Patent: Dec. 11, 2012

(54) TWIN TRANSDERMAL DRUG DELIVERY PATCH

(75) Inventors: Hashem Heitai, San Diego, CA (US); Ludwig J. Weimann, San Diego, CA (US)

(73) Assignee: Pharmapatch, LLC, San Diego, CA (US)

( * ) Notice: Subject to any disclaimer, the term of this patent is extended or adjusted under 35 U.S.C. 154(b) by 345 days.

(21) Appl. No.: 12/564,808

(22) Filed: Sep. 22, 2009

(65) Prior Publication Data

US 2010/0076387 A1 Mar. 25, 2010
US 2010/0222751 A2 Sep. 2, 2010

Related U.S. Application Data

(60) Provisional application No. 61/099,312, filed on Sep. 23, 2008.

(51) Int. Cl.
*A61F 13/00* (2006.01)

(52) U.S. Cl. ........................ 424/443; 424/448

(58) Field of Classification Search ........................ None
See application file for complete search history.

(56) References Cited

U.S. PATENT DOCUMENTS

| | | | |
|---|---|---|---|
| 5,629,014 A | 5/1997 | Kwiatek et al. |
| 5,891,463 A | 4/1999 | Bello et al. |
| 6,277,401 B1 | 8/2001 | Bello et al. |

FOREIGN PATENT DOCUMENTS

WO  WO 93/18727  *  9/1993

* cited by examiner

*Primary Examiner* — Michael G Hartley
*Assistant Examiner* — Robert Cabral
(74) *Attorney, Agent, or Firm* — Buskop Law Group, PC; Wendy Buskop

(57) ABSTRACT

A transdermal drug delivery device is shown and described. The device includes an occlusive or non-occlusive backing, an adhesive, at least one drug delivery region, an adhesive, and a release liner. The device has an open configuration and a closed configuration. When the device is in the closed configuration, the adhesive, the at least one drug delivery region, and the release liner are disposed between first and second portions of the backing.

7 Claims, 11 Drawing Sheets

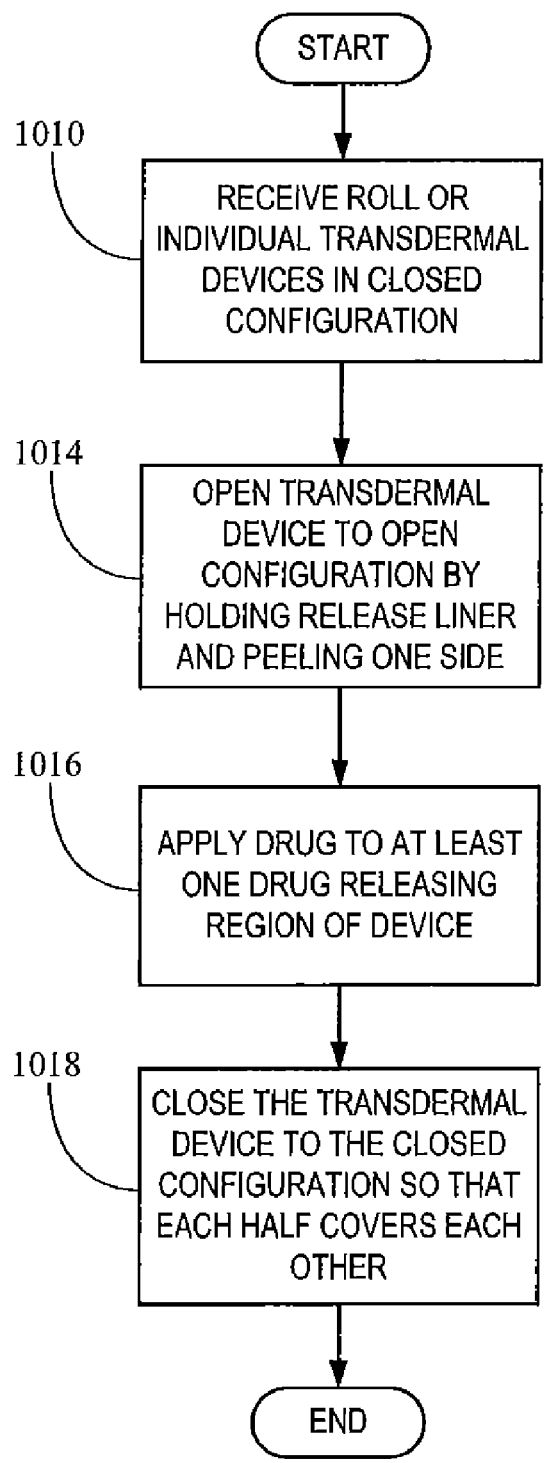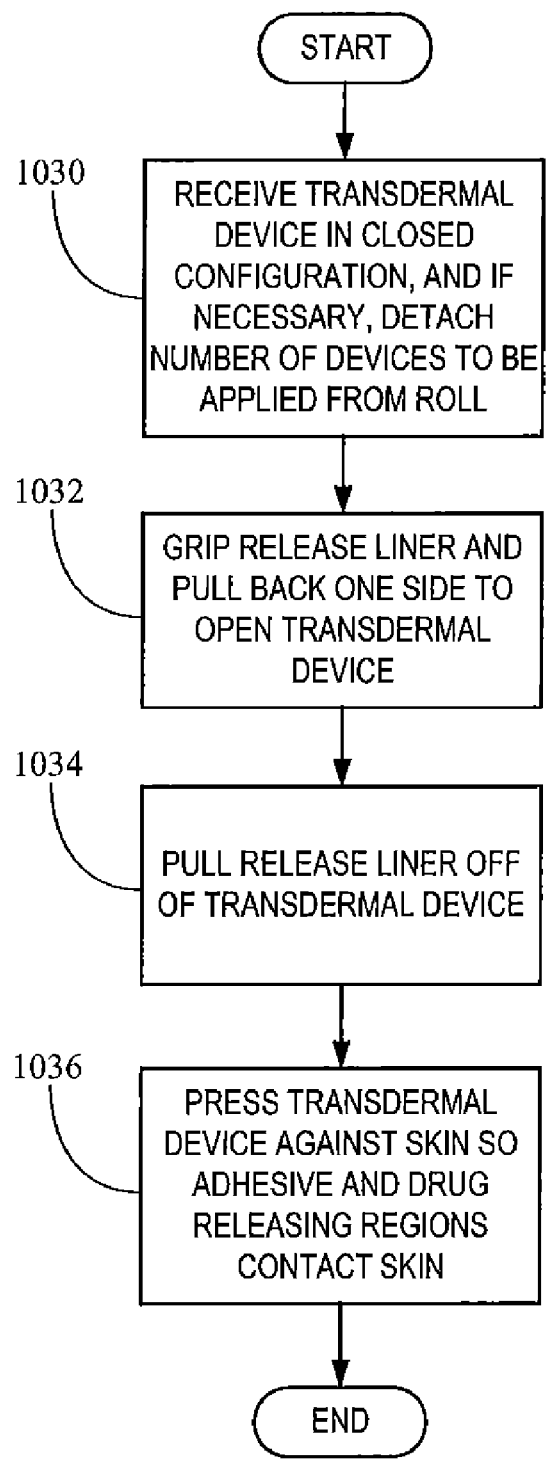
FIG. 3
FIG. 4

TWIN TRANSDERMAL DRUG DELIVERY PATCH

CROSS-REFERENCE TO RELATED APPLICATIONS

This application claims the benefit of U.S. Provisional Patent Application No. 61/099,312, filed Sep. 23, 2008, the entirety of which his hereby incorporated by reference.

TECHNICAL FIELD

The disclosure generally relates to transdermal drug delivery devices, and in particular, to transdermal drug delivery devices that can be manufactured without a drug, transported to another site such as a pharmacy or manufacturing facilities and then loaded with active ingredients. The disclosure also relates to a transdermal delivery device with folded and open configurations.

BACKGROUND

Use of creams and ointments containing active ingredients are a popular means of dermal treatment of not only skin ailments but also for providing an alternative way of delivering drugs either locally or even systemically. Examples include creams for arthritis pain which contain Diclofenac or Ketorolac, creams for aching muscles which contain methyl salicylate and menthol, and creams containing hormones such as estrogens and testosterone for systemic delivery through skin and etc. Specialty creams ordered by physicians are easily prepared (compounded) by a pharmacist right in the pharmacy. However, such combinations of semi-solid materials and an active ingredient are often applied non-uniformly and in a manner that fails to regulate delivery of the active ingredient to the skin in a controlled manner. In addition, exposing the vehicle and active ingredient directly to the atmosphere tends to slow the diffusion of the active ingredient into the skin due to loss of moisture or evaporation of volatile penetration enhancers such as alcohol in the vehicle.

Transdermal drug delivery devices in the form of patches have been used to facilitate the delivery of active ingredients through the skin. There are generally two types of such patches. In the "reservoir" style patch, the active ingredient is disposed in a reservoir on the patch and is not mixed in with the adhesive. The reservoir is disposed on a backing to which a skin adhesive is applied. A membrane overlies the reservoir, and a release liner is placed over the membrane, adhesive, and reservoir. The membrane prevents the release liner from removing the active ingredient from the reservoir when the release liner is removed. However, the membrane also limits the rate of diffusion of the active ingredient into the skin.

In the "monolithic" or "drug-in-adhesive" style of patch, the adhesive and active ingredient are mixed together, possibly with other components such as plasticizers, excipients, and penetration enhancers. The combination of adhesive and active ingredient is applied to a backing, and there is no separate reservoir that includes the active ingredient. A release liner is typically provided over the combination of adhesive/active ingredient when the patch is being stored or transported for later use. Monolithic patches are only suitable for use with active ingredients that can be solubilized by suitable skin contact adhesives and in some cases require other components such as stabilizers to prevent precipitation of the drug from the drug-in-adhesive matrix. In addition, there is a variety of active ingredients for which the manufacture of pre-loaded transdermal drug delivery devices is not currently economically feasible. Thus, a need has arisen for a transdermal drug delivery device that addresses the foregoing issues.

SUMMARY

A transdermal drug delivery device is provided which comprises a backing, an adhesive, at least one drug delivery region, and a release liner. The device has an open configuration and a closed configuration. When the device is in the closed configuration, the adhesive, the at least one drug delivery region, and the release liner are disposed between first and second portions of the backing.

A method of loading a transdermal drug delivery device with a drug for delivery through a patient's skin is provided wherein the device includes a backing, an adhesive, at least one drug delivery region, and a release liner. The device has an open configuration and a closed configuration. When the device is in the closed configuration, the adhesive, the at least one drug delivery region, and the release liner are disposed between first and second portions of the backing. The method comprises opening the transdermal drug delivery device to place the device in the open configuration, applying a drug to the at least one drug delivery region, and closing the transdermal drug delivery device to place the device in the closed configuration.

A method of using a transdermal drug delivery device to deliver a drug through a user's skin is provided wherein the device includes a backing, an adhesive, at least one drug delivery region having a drug disposed therein, and a release liner. The device has an open configuration and a closed configuration. When the device is in the closed configuration, the adhesive, the at least one drug delivery region, and the release liner are disposed between first and second portions of the backing, and the device is provided to the user in the closed configuration. The method comprises opening the transdermal drug delivery device from the closed configuration to the open configuration such that the release liner is disposed on one region of the transdermal drug delivery device, removing the release liner, and applying the transdermal drug delivery device to the user's skin such that the adhesive contacts the user's skin and the at least one drug delivery region contacts the user's skin.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 3 is a flow chart illustrating a method of loading a transdermal drug delivery device;

FIG. 4 is a flow chart illustrating a method of using a transdermal drug delivery device to deliver a drug or other active ingredient through a user's skin;

DETAILED DESCRIPTION

As discussed in detail below, transdermal drug delivery devices of the type described herein have an open and closed configuration wherein when the device is in the closed configuration, a release liner is sandwiched between first and second portions of the backing, and preferably, between first and second portions of adhesive applied to the backing. The transdermal drug delivery devices may advantageously be stored and transported in an unloaded condition to a manufacturer, pharmacist or other health care professional who can then load them with a desired active ingredient. The devices further allow for the transdermal delivery of many drugs for which the economic incentives to provide pre-loaded devices are currently insufficient.

Figure 1A:
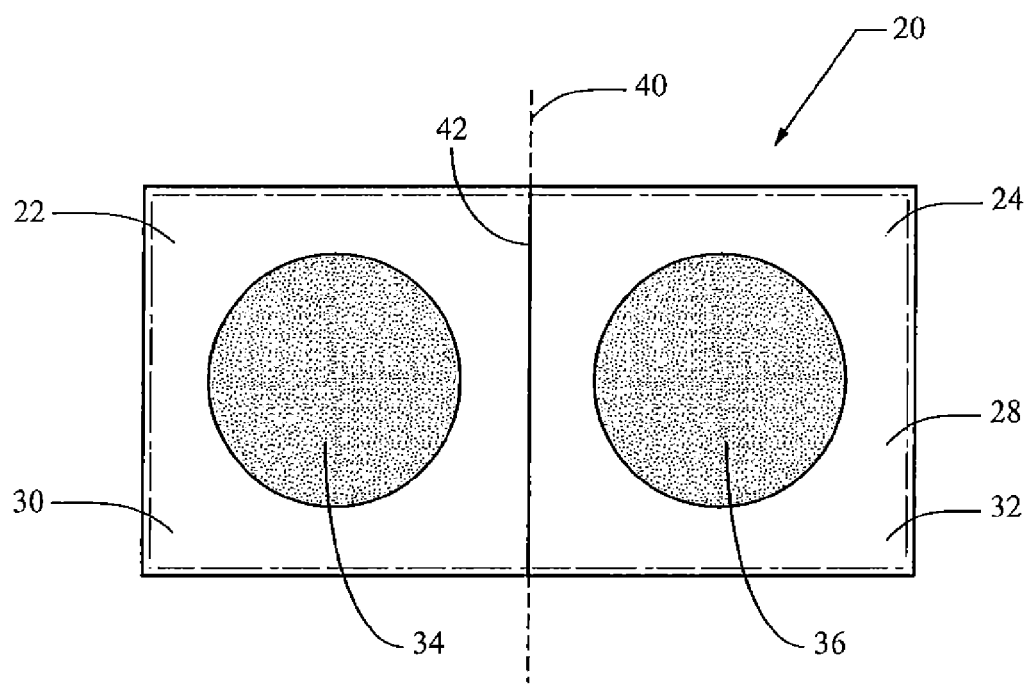
FIG. 1A is a top plan view of a transdermal drug delivery device in an open configuration.
Figure 1B:
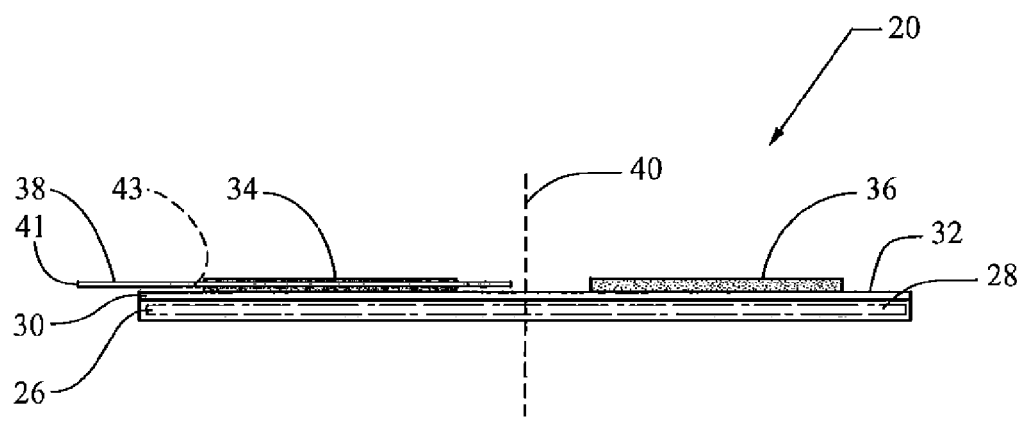
FIG. 1B is a side elevation view of the transdermal drug delivery device of FIG. 1A in an open configuration.
Figure 2A:
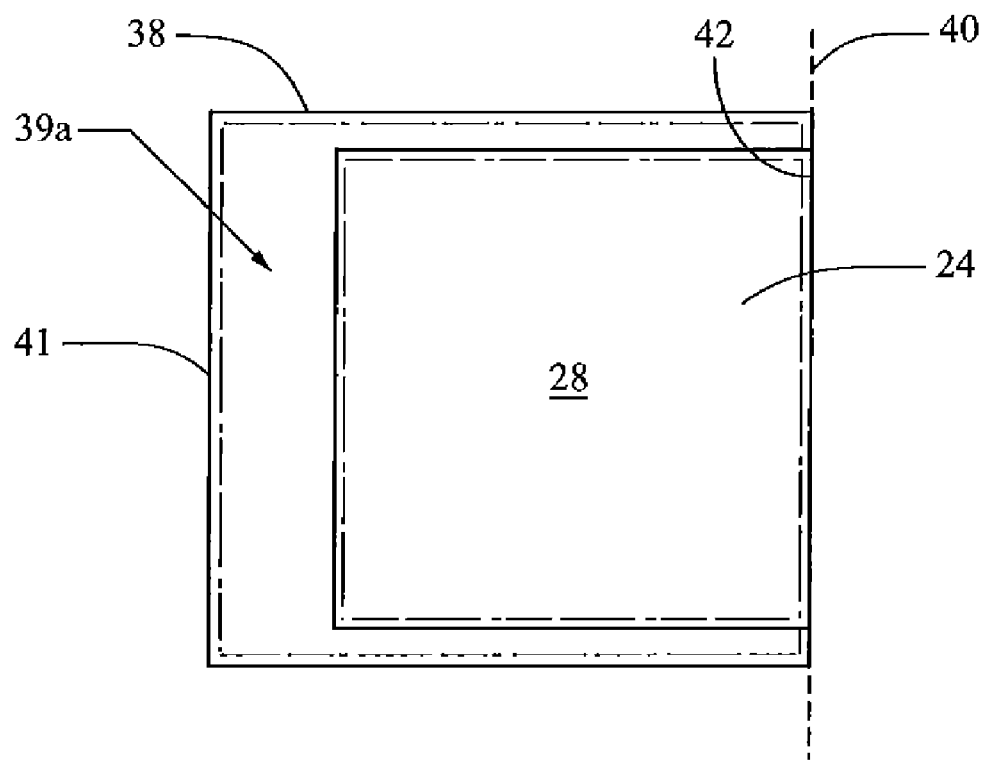
FIG. 2A is a top plan view of the transdermal drug delivery device of FIGS. 1A and 1B in a closed configuration.
Figure 2B:
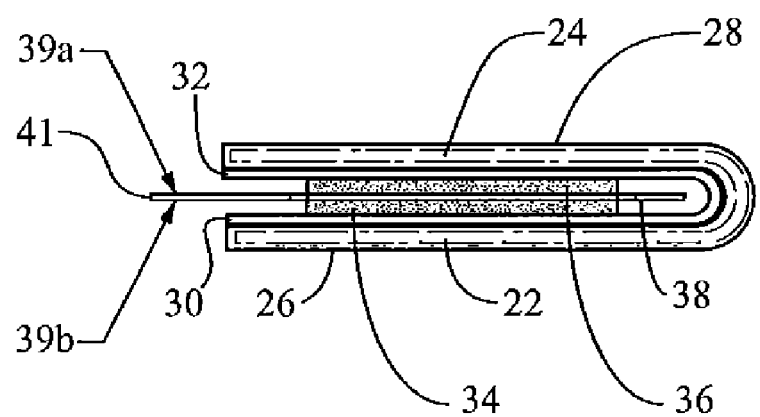
FIG. 2B is a side elevation view of the transdermal drug delivery device of FIGS. 1A and 1B in a closed configuration.

Referring to FIGS. 1A and 1B, transdermal drug delivery device 20 is illustrated in an open position. The same device 20 is depicted in the closed configuration in FIGS. 2A and 2B. Transdermal drug delivery device 20 comprises first section 22 adjacent second section 24. First section 22 and second section 24 are separated by a hinge 42 which allows first section 22 to be folded with respect to second section 24. Folding plane 40 is substantially parallel to and preferably coplanar with hinge 42 and defines an axis about which the first and second sides 22 and 24 are folded when device 20 is in the closed configuration, as shown in FIGS. 2A and 2B.

First section 22 comprises first backing section 26 which is adjacent second backing section 28. First backing section 26 is separated from second backing section 28 by a folding plane 40. In one preferred embodiment, first backing section 26 and second backing section 28 define a uniform, single backing that is separated by folding plane 40. However, the first and second backing sections may be joined by a connector or a connecting material to yield a non-uniform backing. In an especially preferred embodiment, a hinge 42 is provided, such as by applying heat or pressure or by thinning the backing between first backing section 26 and second backing section 28.

Suitable backings include both occlusive and non-occlusive films and foams, preferably those which substantially conform to the user's body when placed on the skin and which are dimensioned and constructed of materials that can readily withstand folding about plane 40. In certain illustrative implementations, first and second backing sections 26 and 28 have a thickness of at least about 0.5 mm, more preferably at least about 0.7 mm, and most preferably at least about 0.8 mm. Thicknesses of no more than about 1.5 mm are preferred, and thicknesses of no more than about 1.0 mm are most preferred.

Transdermal drug delivery device 20 also includes first pressure sensitive adhesive 30 applied on first backing section 26 and second pressure sensitive adhesive 32 applied on second backing section 28. First and second pressure sensitive adhesives 30 and 32 may be the same or different but are preferably the same. In one embodiment, first and second pressure sensitive adhesives 30 and 32 abut one another at folding plane 40 and are substantially uniform across folding plane 40. However, there may also be an adhesive gap across folding plane 40 and hinge 42. First and second pressure sensitive adhesives 30 and 32 can be selected from any of the known and conventional medical grade adhesives, e.g., those based on polyacrylic, polyisobutylene, polyvinylether, silicon, or polyurethane resins. The adhesive sections 30 and 32 are preferably formulated and applied to ensure that the force necessary to remove device 20 from a user's skin is less than the force required to peel first reservoir 34 from first adhesive 30 and the force required to peel second reservoir 36 from second adhesive 32, respectively.

Certain commercially supplied foams and tapes are supplied as an adhesive/backing combination and may be used to provide first backing section 26/first adhesive 30 and second backing section 28/second adhesive 32. Suitable materials include polyethylene and polyolefin foams tapes. Exemplary foam tapes include the polyolefin foam tape supplied under the name CoTran 9773 by 3M of Minneapolis, Minn. and polyvinyl chloride tapes supplied under the name CoTran 9772L by 3M. CoTran 9773 is a polyolefin foam tape laminated with a high tack, acrylate pressure sensitive adhesive. CoTran 9772L is a polyvinyl chloride foam tape laminated with a medium tack, acrylate pressure sensitive adhesive.

Transdermal drug delivery device 20 preferably has a first drug delivery region 34 that is spaced apart from second drug delivery region 36 when device 20 is in the open configuration of FIGS. 1A-B. Transdermal drug delivery device 20 may also comprise more than two (2) drug delivery regions. In the embodiment of FIGS. 1A-B and 2A-B, the first and second drug delivery regions 34 and 36 are first and second reservoirs. First reservoir 34 is adhered to first backing section 26 by first adhesive 30, while second reservoir 36 is adhered to second backing section 28. However, the reservoirs may also be attached to the backing by other, conventional means. As indicated in FIGS. 1A-B, reservoirs 34, 36 preferably each have an area that is less than that of their respective backing sections, 26 and 28. In FIGS. 1A and 2A, reservoirs 34 and 36 are circular. However, a wide variety of geometries may be used, including regular and irregular polygons, ovals, ellipses, triangles, etc.

First reservoir 34 and second reservoir 36 preferably each comprise an absorbent material that is capable of holding a quantity of a drug formulation. As used herein, the term "drug" refers to any active ingredient that may be delivered transdermally to perform a desired therapeutic function. The drug formulation may comprise an active ingredient and may also comprise a semi-solid vehicle. Suitable reservoir materials include open cell foams, woven materials, non-woven materials, cellulosic materials, microporous films, and inherently absorbent materials. If open cell foams are used for first reservoir 34 and/or second reservoir 36, they are preferably open cell foams having at least from about 30 cells/inch to about 120 cells/inch, preferably from about 50 cells/inch to about 90 cells per inch, and more preferably from about 60 cells/inch to about 80 cell/inch. Preferred inherently absorbent materials include cellulosic materials such as paper or microporous films supplied by DSM Solutech under the name Solupor® which has 0.5 micron pores.

In the case of foam reservoirs, preferred foams are open cell, flexible, oleophilic foams that provide a stable matrix for the drug and an oleophilic delivery vehicle. The term "stable matrix" means that property of the foam which, owing to its oleophilic character, enables the foam to function not only as a depot, or reservoir, for the oleophilic drug composition, but also to confine the composition to reservoirs 34 and 36 to prevent or inhibit migration of the drug composition into first and second adhesives 30 and 32 where it could destroy or impair the effectiveness of the adhesives 34 and 36 in securing the drug delivery device 20 to the skin.

In general, the useful foams possess a density of from about 0.8 lb/ft$^3$ to about 8.0 lb/ft$^3$ and preferably from about 1.2 lb/ft$^3$ to about 4.8 lb/ft$^3$. The foam pore density in pores per inch ("ppi") is generally from about 30 ppi to about 120 ppi and preferably from about 60 ppi to about 90 ppi. The foam and can be fully or partially reticulated or nonreticulated. The average thickness of the foam layer can vary from about 30 mils to about 100 mils and for many applications is preferably from about 40 mils to about 70 mils. Suitable reservoir foams that can be employed herein include the untreated oleophilic (i.e., hydrophobic) open cell polyurethane foams disclosed in U.S. Pat. No. 5,352,711, the contents of which are incorporated by reference herein.

Transdermal drug delivery device 20 also includes a release liner 38 which comprises a film that facilitates the storage and opening of transdermal drug delivery device 20 from the closed configuration of FIGS. 2A and 2B to the open configuration of FIGS. 1A and 1B. In the embodiment of FIGS. 1A-B and 2A-B, release liner 38 is a single sheet of film that has a central opening 43 of an area that is substantially equal to or slightly greater than the area of first reservoir 34 and second reservoir 36. Release liner 38 is preferably positioned on first section 22 such that first reservoir 34 projects through the release liner opening 43 and such that release liner 38 does not cover either first reservoir 34 or second reservoir 36 when device 20 is in the closed configuration (FIGS. 2A-B). As will be explained below, the use of this release liner configuration prevents the release liner 38 from contacting the skin contact surfaces of reservoirs 34, 36 and prevents loss of active ingredients when release liner 38 is removed from device 20. As best seen in FIGS. 2A and 2B, release liner 38 is preferably sized to have a length and/or width that is greater than the corresponding length and/or width of both first section 22 and second section 24, thereby providing a projecting edge 41 which a user can manipulate to open device 20 from the closed configuration of FIGS. 2A and 2B to the open configuration of FIGS. 1A and 1B. As shown in FIG. 1B, release liner 38 is preferably sized to cover only one section (22 or 24) of transdermal drug delivery device 20 when device 20 is in the open configuration of FIGS. 1A and 1B.

In certain illustrative embodiments, release liner 38 comprises a polyethylene terephthalate ("PET") film or paper with a release coating on each of its sides 39a and 39b. The release coating preferably provides sufficient adhesion to remain in place on first backing section 26 when device 20 is in the open configuration but allows the user to remove it without removing substantial quantities of first adhesive 30 from first backing section 26 or second adhesive 32 from second backing section 28. Preferred release coatings include silicone release coatings. Release liner 38 preferably has a thickness ranging from about 50 microns to about 200 microns and which is more preferably from about 100 microns to about 150 microns.

In certain illustrative implementations, first adhesive 30 and second adhesive 32 may comprise a silicone adhesive gel such as "Oleeva", a product of Bio Med Sciences of Allentown, Pa. The silicone gel allows transdermal device 20 to be folded and unfolded between the closed and open configurations without requiring the use of a separate release liner and release coating.

Referring to FIGS. 2A and 2B, transdermal drug delivery device 20 is depicted in the closed configuration in which it is folded about folding plane 40 via hinge 42. Hinge 42 is preferably a foldable region of device 20. In one illustrative application, hinge 42 comprises a thinned area of backing between first backing section 26 and second backing section 28 which allows device 20 to be folded. However, depending on the materials selected, the backing need not be thinned. In a preferred embodiment, hinge 42 is created by applying pressure or heat to device 20 along folding plane 40. As shown in FIG. 2B, first reservoir 34 and second reservoir 36 preferably have substantially the same surface area and are preferably in substantial alignment and abutment with one another when device 20 is in the closed configuration. The opening 43 in release liner 38 is preferably sized and positioned to accommodate reservoirs 34 and 36 which are preferably placed in substantially facing opposition to one another. This configuration advantageously prevents the reservoirs 34 and 36 from contacting release liner 38 which can contaminate the drug contained in reservoirs 34 and 36 with release coating on the release liner 38. This configuration also prevents removal of active ingredient from reservoirs 34 and 36 when the release liner 38 is removed from device 20. In addition, if reservoirs 34 and 36 were to contact release liner 38, some amount of the drug could diffuse out of the reservoir and into the release coating, leading to undesirable loss of potency.

As is known to those skilled in the art, many known reservoir style transdermal drug delivery devices require a membrane that is sandwiched between the release liner and the reservoir to avoid such contamination. The membrane disadvantageously slows the diffusion of the drug to the user by adding another layer through which mass transport must occur. Thus, the transdermal drug delivery device 20 of FIGS. 1A-B and 2A-B eliminates the need for a separate membrane that isolates the drug in reservoirs 34 and 36 from the coating on release liner 38. When device 20 is in the closed configuration, any diffusion of the drug from reservoirs 36 and 34 will most likely occur between the reservoirs, thereby minimizing any net loss of the active ingredient available for transdermal delivery to the user.

Referring again to FIGS. 2A and 2B, in the depicted closed configuration, release liner 38 is sandwiched between first and second adhesives 30 and 32 and between first and second backing sections 26 and 28. Side 39a of release liner 38 is coated with a release coating that is in contact with second adhesive 32 while side 39b of release liner 38 is coated with a release coating of the type described previously that is in contact with first adhesive 30. For ease of viewing, the contact between release liner side 39a and second adhesive 32 is not shown in FIG. 2B. Nor is the contact between release liner side 39b and first adhesive 30 shown. The release coating applied to sides 39a and 39b of release liner 38 is preferably compatible with first adhesive 30 and second adhesive 32 to prevent any undesirable interactions which would degrade the performance of the coating or adhesives.

Figure 9:
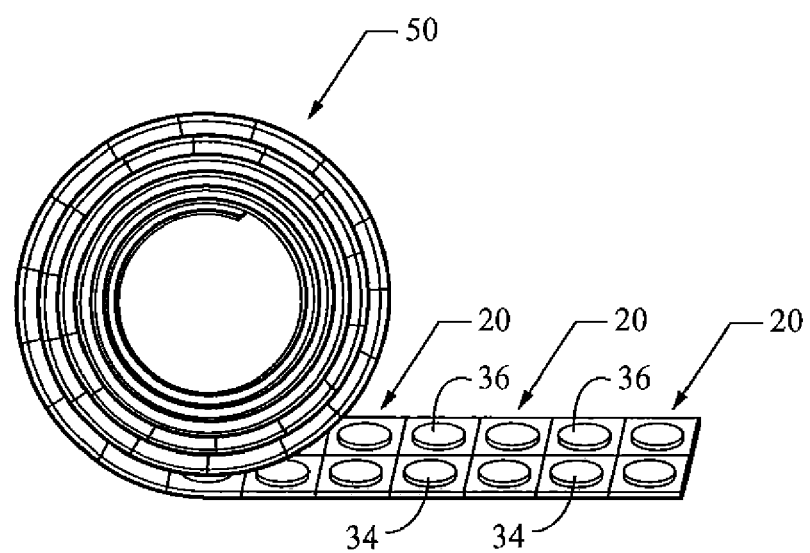
FIG. 9 is a side elevation view of a roll of transdermal drug delivery devices in a closed configuration.
Figure 10:
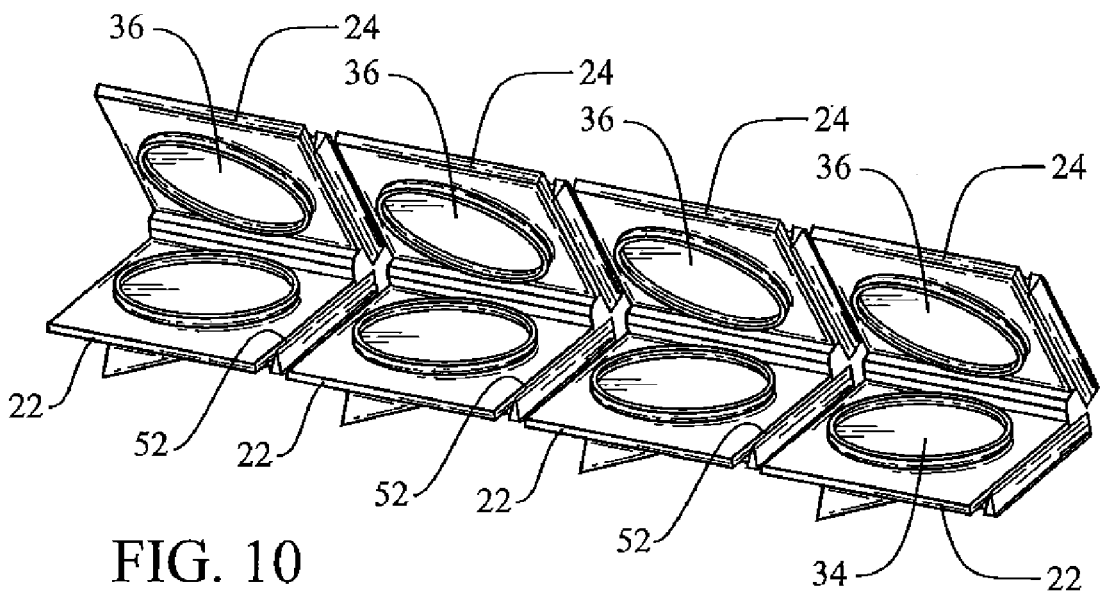
FIG. 10 is a perspective view of four transdermal drug delivery devices in a partially open configuration.

One advantage of the transdermal drug delivery device 20 of FIGS. 1A-B and 2A-B is that it can be stored and transported in an "unloaded" condition (i.e., without a drug or vehicle applied) and a manufacturer, pharmacist or other health care professional can then formulate a selected drug (e.g., a drug prescribed by the user's physician) and/or vehicle and apply it to drug delivery regions 34 and 36 of device 20. In contrast, current transdermal drug delivery devices are pre-loaded at the point of manufacture and cannot be loaded with a selected drug by a third party such as a pharmacist. Referring to FIG. 3 an embodiment of a method of loading a transdermal drug delivery device such as device 20 is provided. In accordance with the method, the pharmacist receives individual transdermal drug delivery devices 20 or a roll of transdermal drug delivery devices 20 (step 1010) such as those depicted in FIG. 9. The roll in FIG. 9 depicts the devices in a closed configuration as viewed from the side. Roll 50 comprises an array of devices in a rolled configuration. The pharmacist then opens the one or more devices 20 by gripping release liner 38 (such as at projecting edge 41 in FIGS. 2A and 2B or tab 41 shown in FIGS. 5 and 10) and pulling first section 22 to one side away from second section 24 (step 1014). FIG. 10 shows a strip of four devices 20 which are in a partially open condition. The same devices are shown in an open condition in FIG. 5. The four devices are each joined by perforations 52 which comprise thinned areas of material that allow the devices 20 to be separated from one another.

Figure 5:
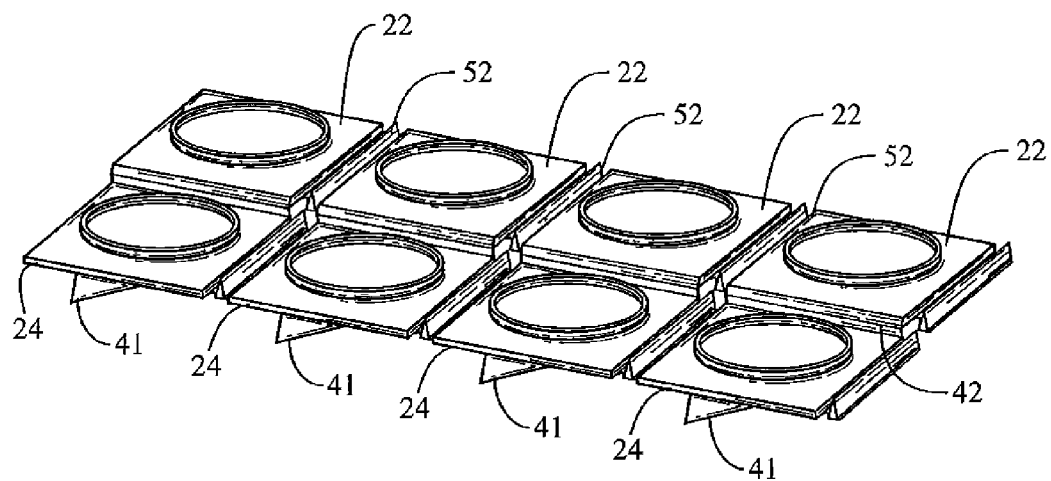
FIG. 5 is a perspective view of a strip of transdermal drug delivery devices in accordance with one style of reservoir.

Once the transdermal drug delivery devices 20 are in the open condition of FIGS. 1A-B and 5, the drug formulation to be delivered to the user is prepared and applied to at least one the drug releasing regions of the device, for example, reservoirs 34 and 36 in the device 20 of FIGS. 1A-B and 2A-B (step 1016). As shown in FIGS. 1A-B, when the drug is being applied to at least one reservoir 34 and 36, release liner 38 stays in place on first adhesive 30 of first section 22, while second adhesive 32 of second section 24 is exposed. Both reservoirs 32 and 34 are exposed when device 20 is in the open configuration.

In one embodiment, the drug formulation is a semi-solid. However, depending on the type of reservoir material used, the drug formulation may also comprise a liquid. For example, in the case of absorbent foam reservoirs, liquid drug formulations may be used because the foam cells act as an absorbent matrix from which the drug can be delivered transdermally.

If a semi-solid drug formulation is required, the active ingredient may be combined with a semi-solid vehicle to provide a semi-solid drug formulation. Suitable semi-solid vehicles include ointments, creams, gels, and low viscosity foams. Examples of suitable semi-solid vehicles include mixtures of water plus thickening agents such as carbomers, poloxamers, poly vinyl povidons, and cellulose derivatives; ointment bases such as lanolin and white petrolatum; emulsions; lotions; and drug suspensions or solutions, e.g. solutions of drug in propylene glycol. These base formulations may also contain penetration enhancers such as lecithin, isopropyl alcohol, propylene glycol.

The active ingredient applied to reservoirs 34 and 36 may include any active ingredient that is suitable treating skin conditions or for delivery through a user's skin and includes all compounds that are lipophilic or non-lipophilic with or without penetration enhancers. The active ingredients may be used for limited duration treatments such as for acute conditions (e.g., athletic injuries) and may also be used to treat systemic conditions. Exemplary active ingredients include anti-inflammatory compounds such as Ketoprofen, Diclofenac, Piroxicam, and Ketorolac, hormones such as estrogens, progesterone, and testosterone, anti-biotics such as Neomycin and polymyxin B, pain management compounds such as lidocaine, ketamine, and morphine, weight loss drugs such as phenteramine, burn treatments; silver sulfadiazine and zinc oxide, tranquilizer/antiemetic; benzodiazepines, veterinary products; methimazol. Other exemplary active ingredients include commercially available brand or generic drugs; hormones (e.g. Androgel); antibiotics such as Neosporin and Polysporin; anti-fungal compounds such as Lamisil and Tolnaftate; and pain medications such as Lidocaine and methylsalicylate.

As mentioned above, the drug formulation applied to reservoirs 34 and 36 may also include penetration enhancers to enhance the penetration of the active compound through the user's skin. One advantage of transdermal drug delivery device 20 is that it facilitates the use of low viscosity penetration enhancers such as alcohols. In known reservoir devices, low viscosity enhancers are often transferred to the release liner adhesive, migrate away from the reservoir and eventually evaporate. However, because reservoirs 34 and 36 are placed in facing opposition to one another and sealed with no release liner placed over either of them, the likelihood of such migration and evaporation is substantially reduced.

After the pharmacist or manufacturing personnel completes the process of preparing the drug formulation and applying it to the drug releasing regions 34, 36 of transdermal drug delivery device(s) 20, he or she closes the device(s) by folding first section 22 about folding plane 40 so that second adhesive 32 is in contact with side 39a of release liner 38 (FIGS. 2A and 2B) (step 1018). Referring to FIGS. 5 and 10, the device(s) 20 may then be separated at perforations 52 prior to being supplied to a user or they may be supplied as an integral strip of devices 20, depending on the user's needs. The devices 20 are then ready to use. The same process could be performed using automated manufacturing equipment in a manufacturing facility.

Referring to FIG. 4, a method of using transdermal drug delivery device 20 is described. The user receives a loaded device 20 (e.g., from a pharmacist) or a plurality of loaded devices in the closed configuration of FIGS. 2A-B. If the user receives a plurality of devices as a strip, then one device 20 is removed via a perforation 52 (see FIG. 5, showing the device in the open configuration). Device 20 is then opened by gripping projecting edge 41 of release liner 38 and peeling back one section (22 or 24) from the other section (step 1032). At this point, device 20 is in the open configuration of FIGS. 1A-B. The user then grips projecting edge 41 of release liner 38 and peels release liner 38 from first adhesive 30 (step 1034). Device 20 is then applied to the skin so that reservoirs 34 and 36 are positioned at the desired location of drug delivery and so that first adhesive 30 and second adhesive 32 are in contact with the user's skin (step 1036). Transdermal drug delivery device 20 is then left in place for a desired duration, e.g., a duration specified by the prescribing physician or the pharmacist. Once the device 20 has been used for the desired duration, the user peels it from the skin and discards it.

Figure 6:
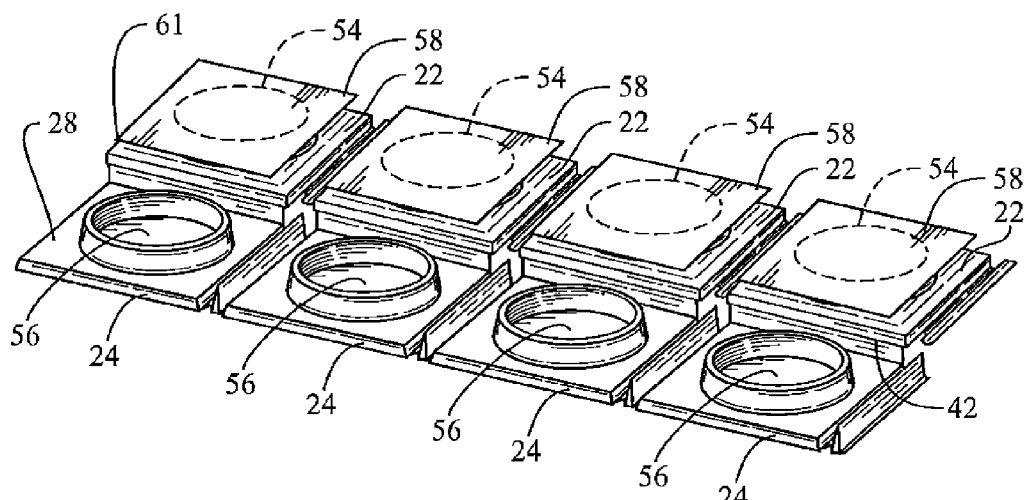
FIG. 6 is a perspective view of a strip of transdermal drug delivery devices in accordance with another style of reservoir.
Figure 7:
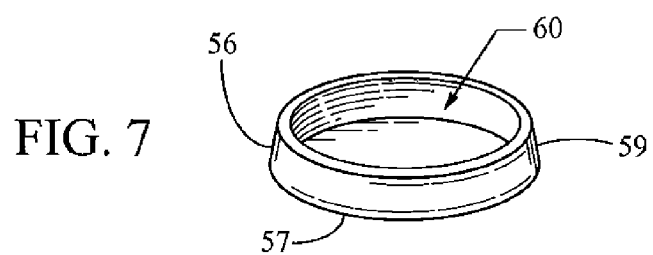
FIG. 7 is a side elevation view of one of the reservoirs of FIG. 6.

In addition to the reservoir materials described above, the drug delivery regions 32 and 34 may comprise solid retainers 54 and 56 as shown in FIGS. 6-7. Retainers 54 and 56 are preferably comprised of a rigid or semi-rigid impermeable material such as plastic or an elastomeric material that is capable of containing a solid or semi-solid composition in its interior. In one illustrative application, a drug formulation comprising a cross-linked polymeric matrix having an active ingredient dispersed therein is contained in retainers 54 and 56. In another example, reactive precursors are placed in retainers 54 and 56 and react in the retainers 54 and 56 to form the cross-linked polymeric matrix. In accordance with the example, placing a mix of two reactive parts inside of the retainer will result in solidified end product containing an active ingredient. For example: Part A and Part B of MED-6345 silicone gel from NuSil Technology may be combined in retainers 54 and 56. In another example, two part thermo-reactive hydrogels from Tyco Healthcare Ludlow are used. In yet another example, UV or radiation solidified compositions like hydrogels from Tyco Healthcare Ludlow and UV solidified hydrogel compositions based on AMPS (2-acrylamido-2 methyl-1-propane sulfonic acid sodium salt) from Lubrizol are used. Other formulations such as cocoa butter (e.g. witepsol) or aqueous polymer solutions (e.g. Hydroxycellulose derivatives) that are solid at lower temperatures but which liquify at higher temperatures e.g. upon skin contact, can also be filled in the retainers. Retainers 54 and 56 may also include a base 57 and may have one or more perimeter walls 59 defining an enclosure in which a drug formulation may be contained. In the embodiment of FIG. 7, retainers 54 and 56 are rings that include a continuous circular perimeter wall 59. However, geometric shapes other than circular shapes may be used, for example, square, elliptical, rectangular, polyhedral, and irregular shapes. Base 57 preferably has an area that is somewhat greater than that of open top surface 60 so that perimeter wall 59 is sloped inwardly from the base 57 towards the open top surface 60. The use of an angled perimeter wall helps retain the drug formulation within retainers 54 and 56. Unlike the embodiment of FIGS. 1A-B, 2A-B and FIG. 5, the release liner 58 may or may not include an opening for accommodating retainers 54 and 56, depending on the nature of the formulation. Release liner 58 preferably comprises the materials described previously with respect to release liner 38 of FIGS. 1A-B and 2A-B and includes a release coating of the type described previously on each of its sides. Release liner 58 also comprises a projecting edge 61 which facilitates opening device 20.

FIG. 6 depicts four side-by-side devices 20 comprising retainers 54 and 56. In FIG. 6, first section 22 is unhinged and removed from second section 24 for ease of viewing. Retainer 54 is visible on the bottom of first section 22 to indicate its location but would likely not be visible (or its outline would only be visible) on an actual device 20. Second section 24 is shown and comprises a second backing section 28 of the type described previously. Second backing section 28 preferably has a second adhesive 32 of the type described previously applied across its surface. Second adhesive 32 is used to adhere device 20 to a user's skin and is also used to adhere retainer 56 to second backing section 28.

Figure 8A:
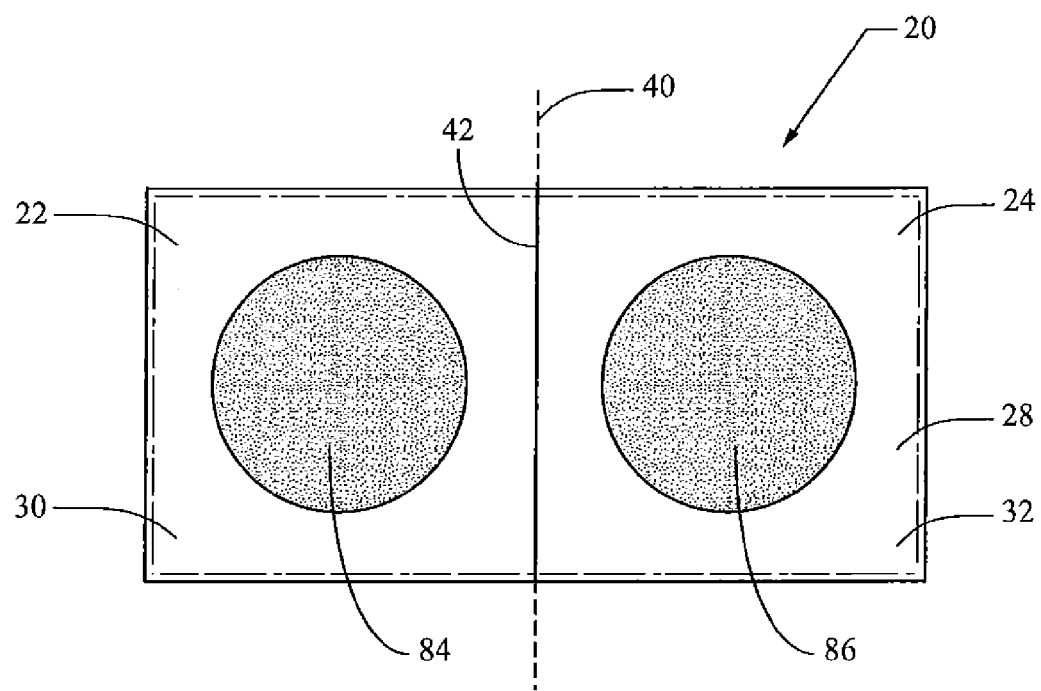
FIG. 8A is a top plan view of a monolithic transdermal drug delivery device with the device in an open configuration.
Figure 8B:
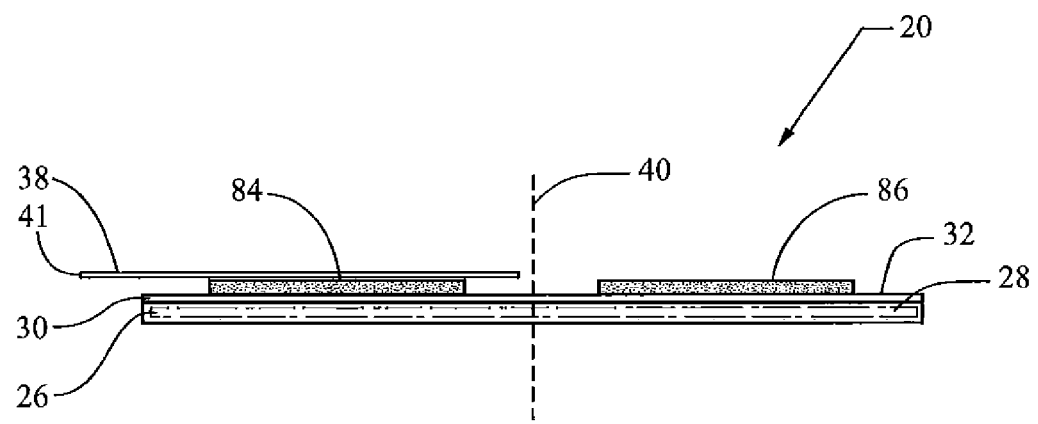
FIG. 8B is a side elevation view of the transdermal drug delivery device of FIG. 8A in an open configuration.
Figure 8C:
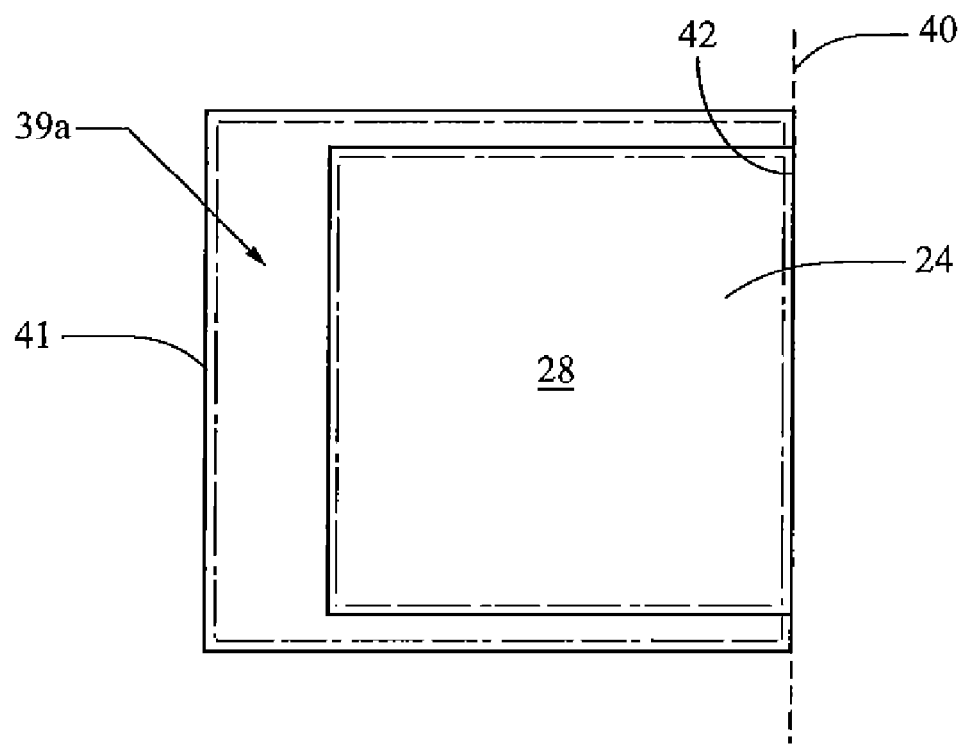
FIG. 8C is a top plan view of the transdermal drug delivery device of FIGS. 8A and 8B in a closed configuration.
Figure 8D:
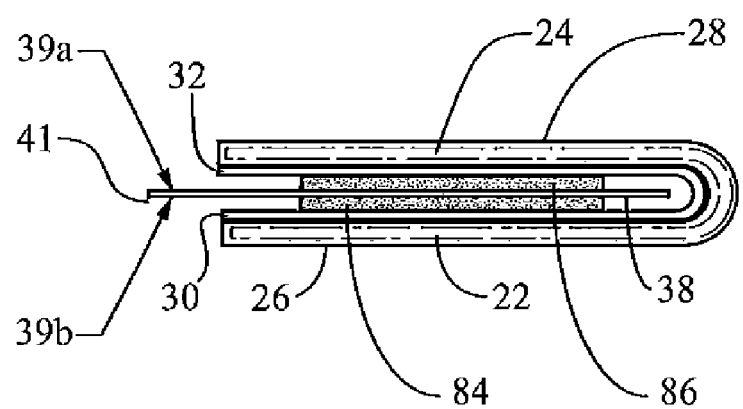
FIG. 8D is a side elevation view of the transdermal drug delivery device of FIGS. 8A and 8B in a closed configuration.
Figure 8E:
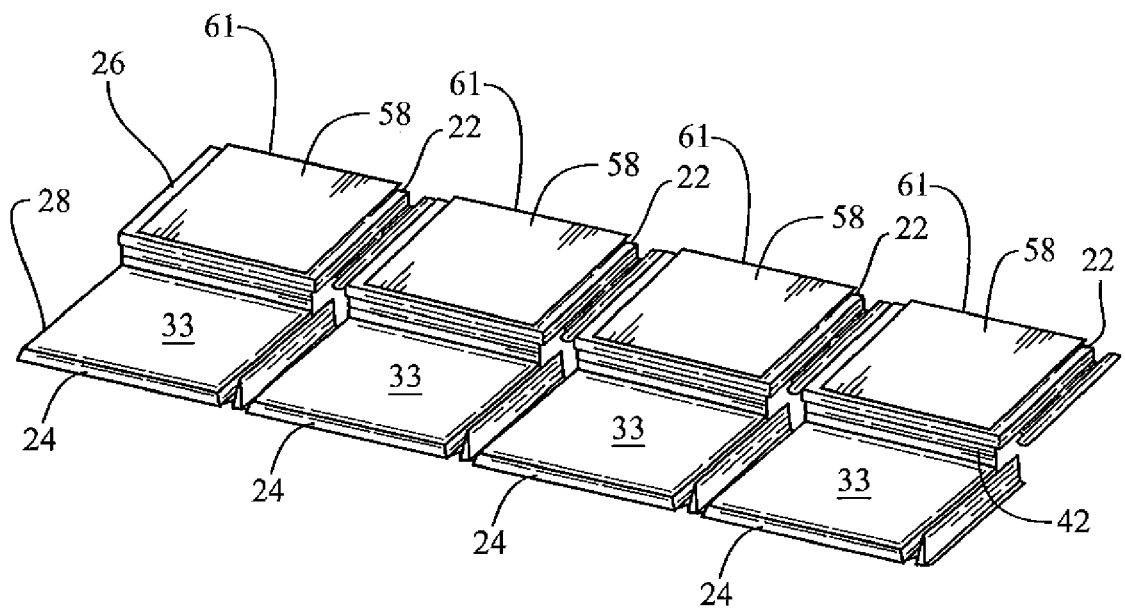
FIG. 8E is a perspective view of a strip of monolithic transdermal drug delivery devices.

Referring now to FIGS. 8A-8D, an embodiment of a monolithic-style transdermal device in accordance with the present disclosure is depicted. The embodiment of FIGS. 8A-8D is similar to that of FIGS. 1A-B and 2A-B and like numerals refer to like elements. However, the transdermal drug delivery device 20 of FIGS. 8A-8D includes monolithic drug delivery regions 84 and 86. One or both of the monolithic drug delivery regions 84 and 86 comprise a combination of skin adhesive and active ingredient. In a preferred embodiment, the skin adhesive component of drug delivery regions 84 and 86 is the same as first pressure sensitive adhesive 30 and second pressure sensitive adhesive 32, respectively. Release liner 38 does not include central opening 43 in this embodiment. Instead, release liner 38 covers first drug delivery region 84 and second drug delivery region 86 (when device 20 is in the closed configuration of FIGS. 8C-8D) to prevent drug delivery regions 84 and 86 from adhering to one another due to their respective adhesive components. Another embodiment of a monolithic-style transdermal drug delivery device 20 is depicted in FIG. 8E In FIG. 8E sections of four devices 20 are shown side-by-side with the first section 22 shown as unhinged and removed from second section 24. The bottom of first section 22 is visible in FIG. 8E. First and second sections 22 and 24 include first and second backing sections 26 and 28, which are of the type described previously. Like the devices 20 of FIGS. 8A-8D, the devices 20 of FIG. 8E are monolithic, i.e., they include a combination of adhesive and active ingredient that is spread across at least a portion of the surface area of first and second backing sections 26 and 28 to define a first monolithic drug delivery region 31 (not shown) in first section 22 and a second monolithic drug delivery region 33 in second section 24. Release liner 58 is of the type described with respect to FIG. 6. Release liner 58 is applied to the monolithic adhesive/drug formulation combination on first section 22 and includes a projecting edge 41 which extends beyond the perimeter of first section 22 to facilitate opening device 20. Monolithic adhesives/drug formulations typically consist of active ingredients dispersed in adhesive matrixes such as acrylic, polyisobutylene rubber and silicone An advantage of the monolithic-style transdermal delivery devices of FIGS, 8A-8E is that they can be transported in a closed configuration, which reduces the required packaging area, and therefore, reduces manufacturing costs.

Figure 11:
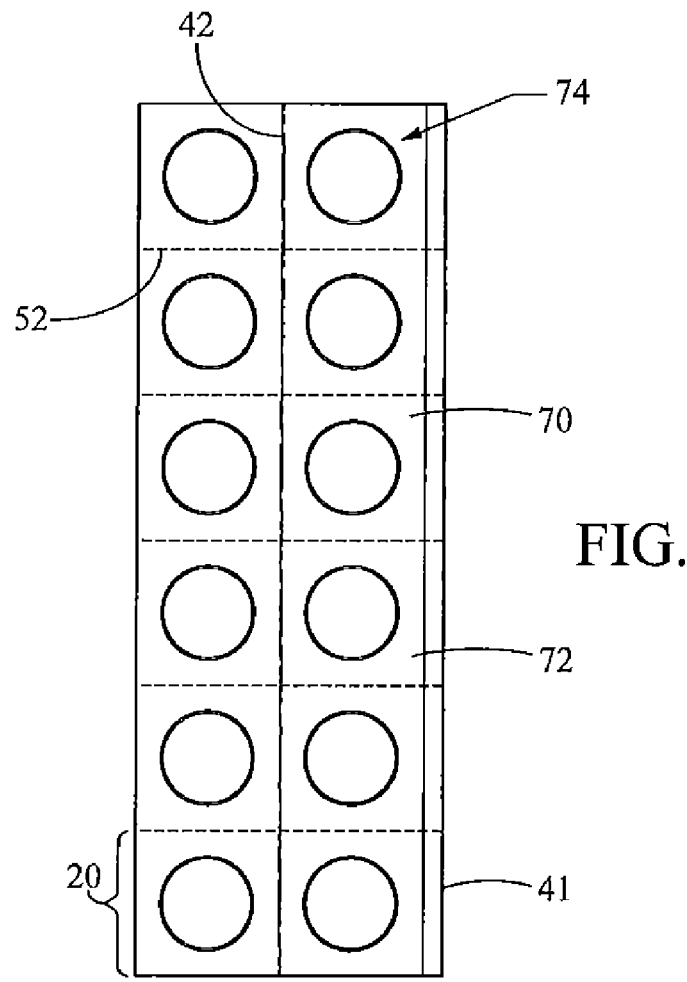
FIG. 11 is a top plan view of a sheet of unloaded transdermal drug delivery devices used to illustrate a method of manufacturing the same.

Referring to FIG. 11, a method of manufacturing transdermal drug delivery device 20 of FIGS. 1A-B and 2A-B will now be described. In accordance with the method, a sheet of backing material 70 used to form backing sections 26 and 28 is provided. The sheet of backing material 70 has an adhesive 72 that defines first and second adhesives 30 and 32 (FIG. 2B). A sheet of the material used to form reservoirs 74 is provided, and individual reservoirs 74 are die-cut to the desired size and shape. Each reservoir 74 is then placed on the adhesive/backing sheet 70, 72 and is spaced apart from one another by a desired distance. Perforations 52 are provided between each adjacent row of reservoirs 74, for example, by using a perforating machine or a heat thinning device. Hinges 42 are defined in sheet 70, for example, by pressure or heat. A release liner sheet (not shown) includes cut-outs sized to accommodate the reservoirs 74. The release liner is preferably sized to provide a projecting edge 41 on each device 20. The resulting strip sheet 41 is folded on the horizontal direction about hinge 42. The folded devices 20 may then be rolled up as shown in FIG. 9 and stored or transported to a manufacturing site, pharmacist or other health care personnel for use as described above with respect to FIG. 3.

Figure 14:
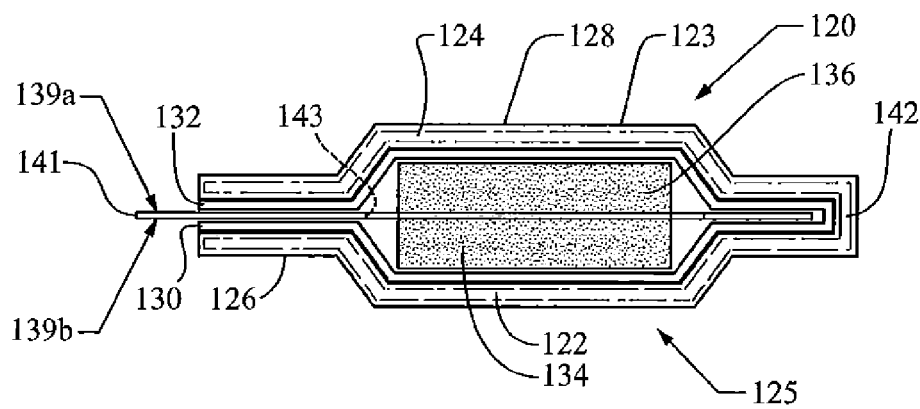
FIG. 14 is a side elevational view of a transdermal drug delivery device having a well in which a drug delivery region is located.

Referring to FIG. 14, an additional embodiment of a transdermal drug delivery device 120 is shown. Transdermal drug delivery device 120 includes first and second sections 122 and 124 with corresponding first and second wells or recessed areas 123 and 125 in which corresponding first and second drug delivery regions 134 and 136 are disposed. The use of first and second wells 123 and 125 allows for an increase in the volume of first and second drug delivery regions 136 and 134, which in turns allow more drug to be held by device 120.

Figure 15:
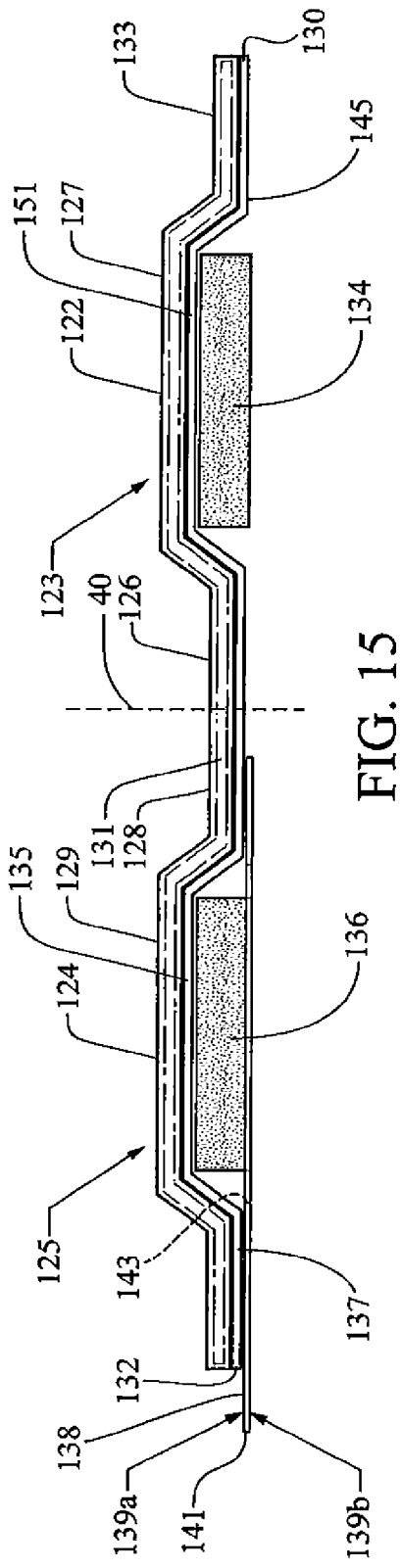
FIG. 15 is a side elevational view of the transdermal drug delivery device of FIG. 14 in an open configuration.
Figure 16:
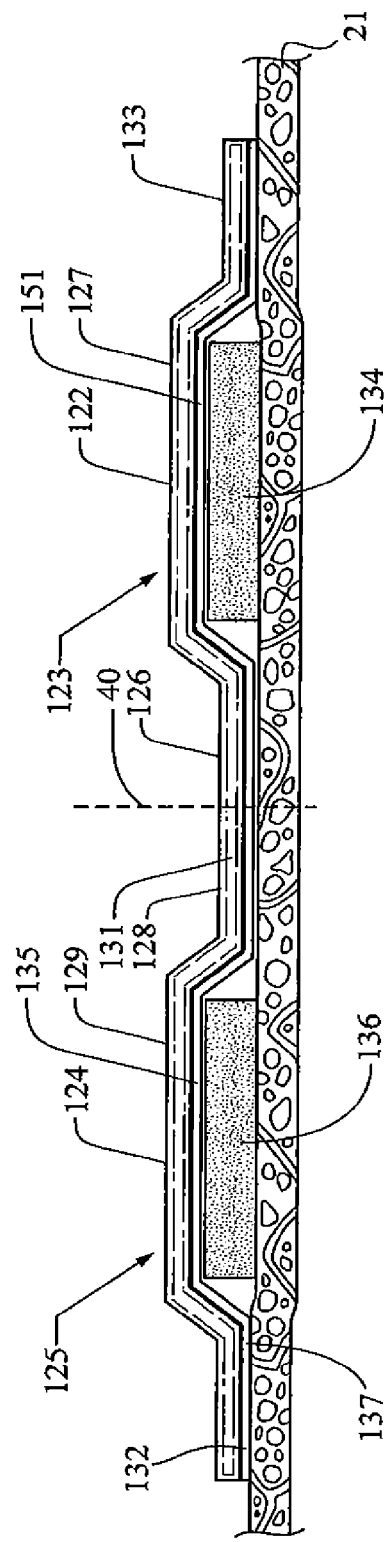
FIG. 16 is a side elevational view of the transdermal drug delivery device of FIG. 15 in an open configuration attached to a user's skin.

As best seen in FIGS. 15 and 16, in one example, first well 123 is provided by recessing a portion of first backing section 126 to create first recessed backing portion 127 and first non-recessed backing portion 133 and by recessing a portion of first pressure sensitive adhesive 130 to create first recessed pressure sensitive adhesive portion 151 and first non-recessed pressure sensitive adhesive portion 145. Second well 125 is similarly created by recessing a portion of second backing section 128 to create second recessed backing portion 129 and second non-recessed backing portion 131 and by recessing a portion of second pressure sensitive adhesive 132 to create second recessed pressure sensitive adhesive portion 135 and second non-recessed pressure-sensitive adhesive portion 137. As indicated in FIGS. 15 and 16, the recessed and non-recessed portions of each of the first and second sections 122 and 124 are spaced apart from one another along the same direction that is parallel to the centerline shown in FIGS. 15 and 16, which is also the direction perpendicular to the user's skin 21 when device 120 is in use (FIG. 16). Similarly, first recessed backing portion 127 is spaced apart from first non-recessed backing portion 133 along a direction parallel to the centerline shown in FIGS. 15 and 16 as are second recessed backing portion 129 and second non-recessed backing portion 131. First recessed pressure sensitive adhesive portion 151 is spaced apart from first non-recessed pressure sensitive adhesive portion 145 along a direction parallel to the centerline, as are second recessed pressure sensitive adhesive portion 135 and second non-recessed adhesive portion 137.

As shown in FIG. 15, release liner 138 of the type described previously is provided and includes a central opening 143 that allows the surfaces of drug releasing regions 134 and 136 to abuttingly contact one another when device 120 is in the closed position of FIG. 14. In the open configuration of FIG. 15, the second non-recessed pressure sensitive adhesive portion 137 is in contact with surface 139a of release liner 138 such that the release liner surface 139a is releasably adhered to second non-recessed pressure sensitive adhesive portion 137. In the closed configuration of FIG. 14, first non-recessed adhesive portion 145 releasably adheres to surface 139b of release liner 138, and drug releasing regions 136 and 138 are substantially aligned and in facing opposition to one another.

As shown in FIGS. 14-16, drug releasing regions 134 and 136 may comprise corresponding reservoirs of the type described previously. In one exemplary embodiment, the reservoirs comprise open cell foams of the type described above. However, other designs such as monolithic designs or the hollow rings described previously may also be used.

Wells 123 and 125 may be formed by a variety of known processes. In one example, a thermoforming process is used. In accordance with the example, pressure sensitive adhesive sections 130 and 132 are applied to their corresponding backing sections 126 and 128 while device 120 is in a flat, preformed condition. A temporary release liner may be applied to the adhesive sections 130 and 132 during the thermoforming process. The flat construct is then applied over a mold that defines the shape of wells 123 and 125 and heated to a temperature sufficient to cause the flat construct to begin to sag. Vacuum (in the case of vacuum thermoforming) or pressure (in the case of pressure thermoforming) is then applied to force the construct against the mold walls, thereby causing the construct to assume the shape of the mold. The temporary release liner is then removed, and drug releasing regions 134 and 136 (e.g., open cell foams) are applied to the recessed pressure sensitive adhesive portions 141 and 135. Release liner 138 is then applied as shown in FIG. 15 and the device 120 is closed. If desired, drug releasing regions 134 and 136 may be filled with a drug as described previously before closing device 120. Alternatively, the device 120 maybe closed to the closed position of FIG. 14 without adding a drug, and the drug may be added later, as described above with respect to the method of FIG. 3. In other examples, backing sections 126 and 128 may be provided as a flat construct prior and thermoformed prior to the application of pressure sensitive adhesives 130 and 132. The adhesives 130 and 132 may then be applied to the thermoformed backing sections 126 and 128. In addition to vacuum and pressure thermoforming processes, twin sheet thermoforming may be used. Materials suitable for such thermoforming processes include both single and co-extruded materials and thermoplastics. Examples of suitable materials include, without limitation, the following: ABS, acrylic polymers, PETG, polycarbonates, polyethylene (HDPE, UHMW), polypropylene, polystyrene, PVC, TPR, and TPO.

EXAMPLES

Example 1

Transdermal Flux for Open and Covered Testosterone Creams

Figure 12A:
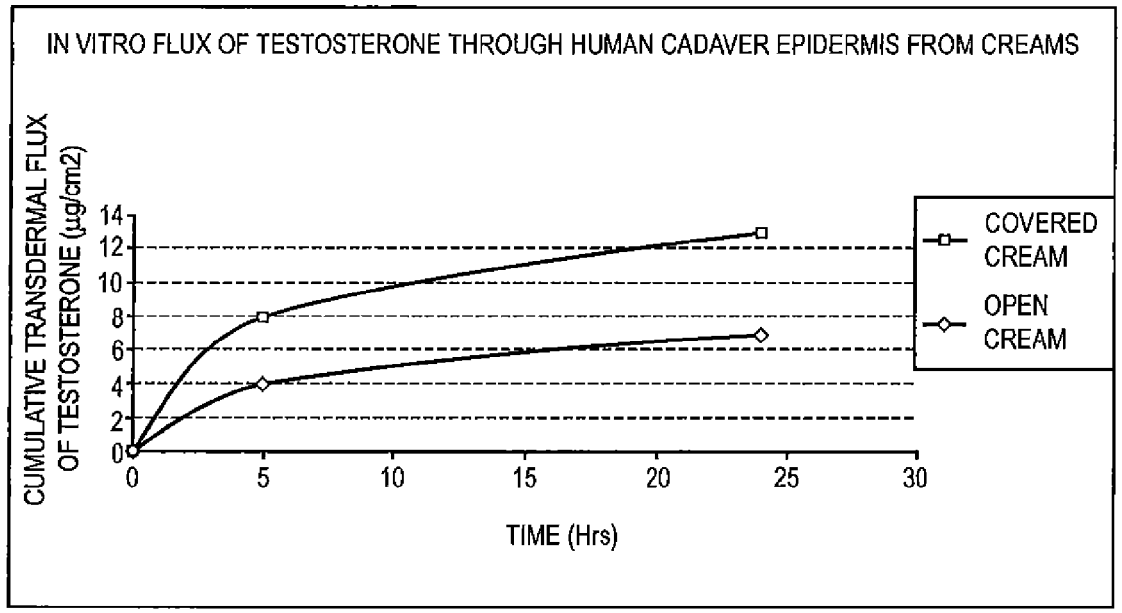
FIG. 12a is a graph depicting transdermal flux data for an open testosterone cream and a testosterone cream covered with an occlusive backing.

As mentioned above, many active ingredients that are of therapeutic interest are not commercially available in transdermal delivery devices. Instead, such active ingredients are compounded with creams or ointments and are applied in an "open" fashion, i.e., they are exposed to the air. To demonstrate the benefits of delivering such active ingredients in a transdermal device, two experiments were conducted in which different formulations were applied to a cadaver skin both as an open cream and as a covered cream, i.e., a cream applied to an occlusive backing. In the first experiment, a cream containing two (2) percent testosterone by weight was placed on a cadaver skin in a Franz cell. In three cells, the cream was exposed to the air and in three other cells, the cream was covered with an occlusive film. The resulting cumulative transdermal flux data in $\mu g/cm^2$ is presented in FIG. 12a. As the data indicates, the covered cream demonstrated a superior transdermal flux throughout the entire time period. After five (5) hours, the occlusive backing device had already achieved a transdermal flux that was twice as high as that of the open cream.

Example 2

Transdermal Flux for Open and Covered Ketoprofen Creams

An experiment similar to that of Example 1 was conducted using a ketoprofen cream. The ketoprofen cream contained ten (10) percent ketoprofen by weight. The cream was applied in an open fashion to cadaver skin in three Franz cells and was applied on an occlusive backing in three other Franz cells.

Figure 12B:
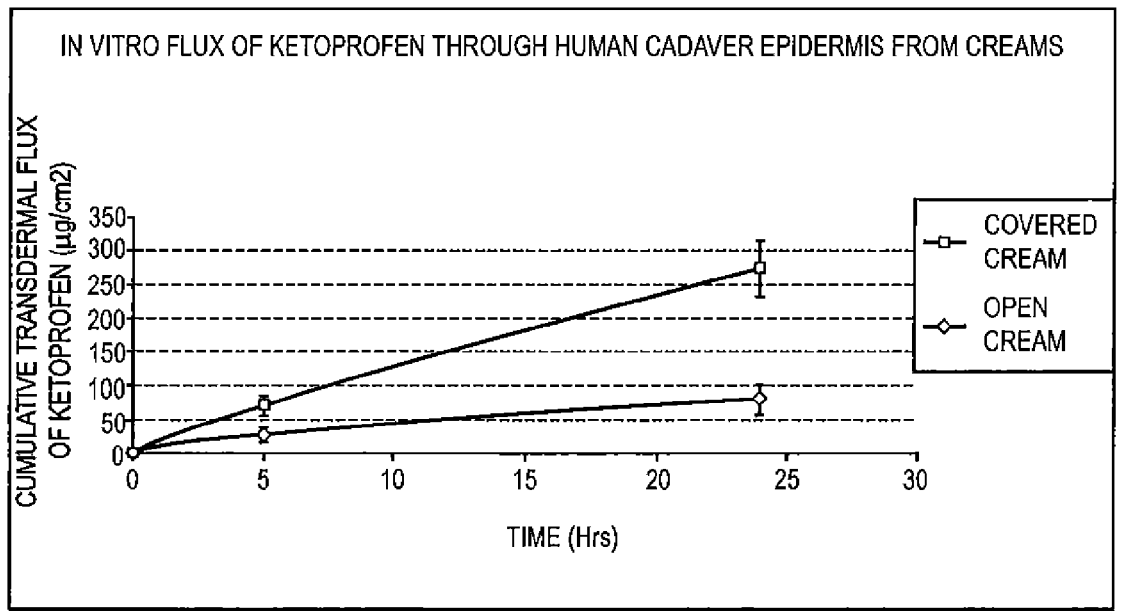
FIG. 12b is a graph depicting transdermal flux data for an open ketoprofen cream and a ketoprofen cream covered with an occlusive backing.

The resulting transdermal flux data is presented in FIG. 12b. As the data indicates, the covered cream demonstrated a superior transdermal flux throughout the entire time period. After five (5) hours, the occlusive backing had already achieved a transdermal flux that was approximately three (3) times as high as the open cream.

Example 3

Transdermal Flux for a Commercial Patch and a Twin Reservoir Patch

As mentioned above, commercially available reservoir style transdermal drug delivery devices include a membrane applied across the reservoir which prevents active ingredient from being removed with the backing when it is peeled off of the device. In contrast, the transdermal drug delivery device of FIGS. 1A-B and 2A-B requires no membrane. To determine the benefits of eliminating the membrane, an experiment was conducted to evaluate the flux of the active ingredient in a commercially available patch and a patch prepared according to FIGS. 1A-B and 2A-B.

Figure 13:
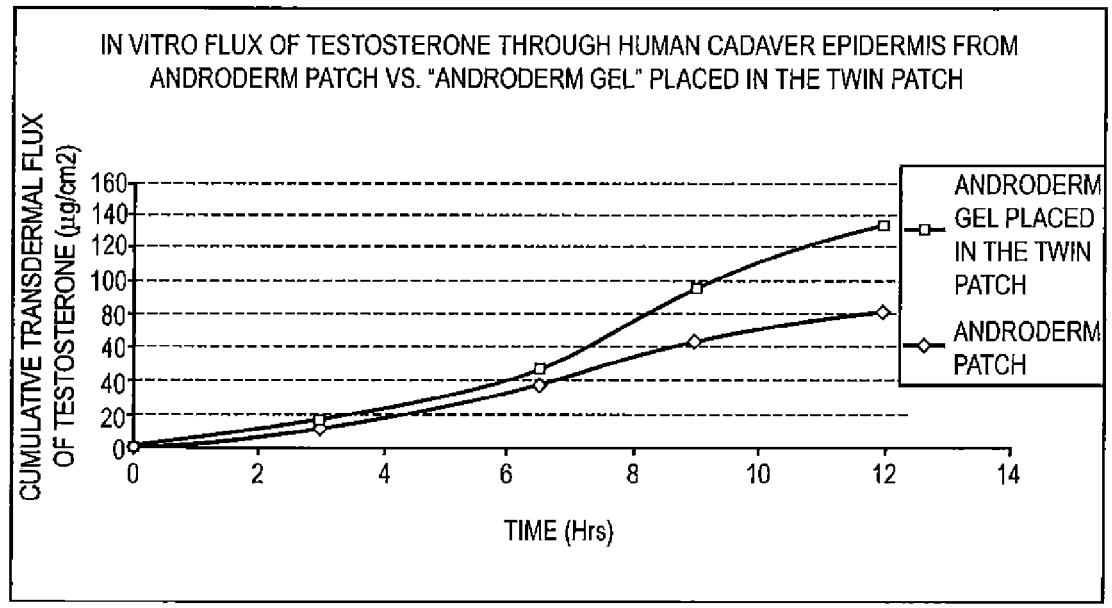
FIG. 13 is a graph depicting transdermal flux data for a commercial transdermal drug delivery device and a twin reservoir transdermal drug delivery device embodying the present invention.

An Androderm testosterone patch (Watson Pharmaceuticals, Inc.) comprising a gel/testosterone mixture was applied to a human cadaver skin and placed in a Franz cell. The patch included one reservoir having an area of 40 cm$^2$. The resulting cumulative flux of testosterone in μg/cm$^2$ was measured and is depicted in the lower graph FIG. 13. The gel/testosterone mixture of an Androderm patch was removed and distributed between two 20 cm$^2$ reservoirs in a patch of the type depicted in FIGS. 1A-B and 2A-B. Unlike the commercial Androderm patch, the twin reservoir patch did not include a membrane over the reservoirs. The twin reservoir patch was applied on a cadaver skin and placed in a Franz cell. The resulting transdermal flux data is depicted in the upper graph in FIG. 13. As FIG. 13 indicates, the twin reservoir patch had approximately the same cumulative transdermal flux as the commercial patch for the first five (5) hours. However, after five (5) hours, the cumulative flux of testosterone from the twin reservoir patch surpassed that of the commercial patch, and after twelve (12) hours, the flux from the twin reservoir patch was at least about 60 percent higher than that of the commercial patch, indicating that the avoidance of a protective membrane layer over the twin patch reservoirs improved the flux of testosterone.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A transdermal drug delivery device, comprising:
   a backing comprising a first section and a second section, wherein the first section comprises a first drug delivery section and the second section comprises a second drug delivery section;
   an adhesive disposed on both the first section and the second section of the backing; and
   a release liner disposed on either the first section or the second section of the backing, wherein the release liner is configured to engage the adhesive on the associated section of the backing while allowing the drug delivery section of the associated section to protrude therethrough;
   wherein the sections of the first drug delivery section and the second drug delivery section are separated from one another in an open configuration and wherein the first drug delivery section and the second drug delivery section are in contact with one another and the release liner engaged with the adhesive on both sections of the backing when the device is in a closed configuration.

2. The transdermal drug delivery device of claim 1, wherein the backing and adhesive define a well, and at least one drug delivery region is located in the well.

3. The transdermal drug delivery device of claim 1, wherein when the device is in the open configuration, the device defines first and second adjacent sections, and the release liner is disposed on the first section but not the second section of the device.

4. The transdermal drug delivery device of claim 1, wherein the at least one drug delivery region comprises first and second drug delivery regions, the first drug delivery region comprises a first reservoir, the second drug delivery region comprises a second reservoir, and when the transdermal drug delivery device is in the open configuration, the first reservoir is spaced apart from the second reservoir.

5. The transdermal drug delivery device of claim 4, wherein at least one of the first and second reservoirs comprises an absorbent material.

6. The transdermal drug delivery device of claim 1, wherein the at least one drug delivery region comprises first and second spaced apart drug delivery regions, and when the device is in the closed configuration, the first drug delivery region contacts the second drug delivery region.

7. The transdermal drug delivery device of claim 1, wherein the device is monolithic.

* * * * *

UNITED STATES PATENT AND TRADEMARK OFFICE
CERTIFICATE OF CORRECTION

| | | |
|---|---|---|
| PATENT NO. | : 8,329,210 B2 | Page 1 of 1 |
| APPLICATION NO. | : 12/564808 | |
| DATED | : December 11, 2012 | |
| INVENTOR(S) | : Hashem Heiati et al. | |

It is certified that error appears in the above-identified patent and that said Letters Patent is hereby corrected as shown below:

On the Title Page, Item (75) the first named Inventor: Hashem Heitai's last name is incorrect, "Heitai" should be deleted and replaced with --Heiati--.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,329,210 B2
APPLICATION NO. : 12/564808
DATED : December 11, 2012
INVENTOR(S) : Hashem Heiati et al.

It is certified that error appears in the above-identified patent and that said Letters Patent is hereby corrected as shown below:

On the Title Page, Item (12), delete "Heitai" and insert --Heiati--.

On the Title Page, Item (75) the first named Inventor: Hashem Heitai's last name is incorrect, "Heitai" should be deleted and replaced with --Heiati--.

This certificate supersedes the Certificate of Correction issued June 17, 2014.

Signed and Sealed this
Fifth Day of August, 2014

Michelle K. Lee
*Deputy Director of the United States Patent and Trademark Office*